(12) United States Patent
Ashkenazi et al.

(10) Patent No.: US 7,576,334 B2
(45) Date of Patent: Aug. 18, 2009

(54) PHOTOACOUSTIC INDICATORS

(75) Inventors: Shai Ashkenazi, Ann Arbor, MI (US); Raoul Kopelman, Ann Arbor, MI (US); Russell S. Witte, Tucson, AZ (US); Thomas D. Horvath, Little Rock, AR (US); Gwangseong Kim, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 12/050,493

(22) Filed: Mar. 18, 2008

(65) Prior Publication Data
US 2008/0230717 A1   Sep. 25, 2008

Related U.S. Application Data

(60) Provisional application No. 60/918,918, filed on Mar. 19, 2007.

(51) Int. Cl.
*G01N 21/64* (2006.01)

(52) U.S. Cl. .................. 250/459.1; 250/458.1

(58) Field of Classification Search .............. 250/459.1, 250/458.1
See application file for complete search history.

(56) References Cited

U.S. PATENT DOCUMENTS

2004/0085540 A1* 5/2004 Lapotko et al. ............. 356/432
2005/0070803 A1* 3/2005 Cullum et al. .............. 600/473

* cited by examiner

*Primary Examiner*—David P Porta
*Assistant Examiner*—Mindy Vu
(74) *Attorney, Agent, or Firm*—Harness, Dickey & Pierce, P.L.C.

(57) ABSTRACT

A method of measuring fluorophore excited state lifetimes comprising initiating an excitation laser pulse at a dye to excite dye molecules of the dye from a ground state to an excited state and initiating a probing pulse at the dye molecules thereby generating a first set of photoacoustic waves at a first time delay resulting in a first intensity point. The process can be repeated, optionally introducing a second excitation laser pulse, to generate a second set of photoacoustic waves at a second time delay resulting in a second intensity point. The data can be analyzed to determine a slope between the first intensity point and the second intensity point.

8 Claims, 5 Drawing Sheets

PHOTOACOUSTIC INDICATORS

CROSS-REFERENCE TO RELATED APPLICATIONS

This application claims the benefit of U.S. Provisional Application No. 60/918,918, filed on Mar. 19, 2007. The disclosure of the above application is incorporated herein by reference.

GOVERNMENT INTEREST

This invention was made with government support under Grant No. DMR 0455330 awarded by The National Science Foundation and Grant No. EB 003455 awarded by The National Institutes of Health. The government has certain rights in the invention.

FIELD

The present disclosure relates to measurement of fluorophore and, more particularly, relates to measurement of fluorescence lifetimes of fluorophore.

BACKGROUND AND SUMMARY

The statements in this section merely provide background information related to the present disclosure and may not constitute prior art.

The measurement of fluorescence lifetime and its application for biology and medicine have been studied intensively. Measuring fluorescence lifetimes of fluorophores provides a sensitive probe of the microenvironments of the fluorophore. Its sensitivity is not affected by the concentration of the fluorophore or by the excitation light intensity. This is particularly significant in biological and clinical applications where dye concentration cannot be precisely controlled and light fluence is highly non-uniform. Optical imaging techniques have been developed to map the distribution of fluorescence lifetime in a wide field of view. These techniques were applied for functional imaging of cellular metabolism, oxygen sensing, mapping the concentration and dynamics of ions such as Ca, and for probing molecular associations by sensing intra-molecular distances. In all these applications the lifetime is evaluated by measuring the decay of the fluorescent signal, or by transient absorption. One of the major difficulties in applying these methods for clinical imaging is the loss of spatial information due to strong light scattering.

According to the principles of the present teachings, a method for local measurement of a dye's excited state lifetime is provided. This method does not require collecting the emitted light but rather relies on photoacoustic probing. This method is demonstrated for oxygen level measurement using oxygen sensitive dye and also for pH imaging using ratiometric photoacoustic chemical sensing.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses.

A. Oxygen Level Measurement Technique

The lifetime of fluorophore's excited state is typically an intrinsic property of the fluorophore, determined by the quantum transition amplitude between the initial and final states. In many cases, interactions with the environment can shorten the unperturbed lifetime. This mechanism forms the basis for a wide range of fluorescent sensors applied to biological systems. A typical example is oxygen sensitive dyes. These dyes can be excited into a triplet state which has a relatively long lifetime due to the "forbidden" (spin flip) nature of the relaxation to the ground state. However, inter-molecular collisions with oxygen (in its triplet ground state) can quench the excited state. Measuring the excited state lifetime provides a quantitative measure of oxygen concentration in the environment. This allows for tissue oxygenation imaging, an extremely valuable tool for cancer diagnostics, assessment of tumor aggressiveness, and treatment monitoring. Lifetime measurement can also be utilized to measure inter-molecular distances based on energy transfer between acceptor and donor molecules (FRET pair). Shorter donor excited state lifetimes can be observed at short intermolecular distances, due to efficient quenching by the acceptor molecule. This "spectral ruler" technique enables monitoring of protein dynamics in living cells.

In these applications, the lifetime is evaluated by measuring the decay of the fluorescent signal. Compared to fluorescent intensity measurements, lifetime measurements are much more robust and stable due to insensitivity to dye concentration, excitation intensity, and light absorption in tissue.

One of the major difficulties in applying these methods for clinical imaging is the loss of spatial information due to strong light scattering. According to the principles of the present teachings, a technique for local measurement of a dye's excited state lifetime is provided—one that does not require collection of the fluorescent emission but rather relies on photoacoustic probing. The technique is based on a double pulse illumination. A first pulse is used to excite the dye and a second pulse is used to generate photoacoustic waves that are collected and provide information on the dye's optical absorption. Since the optical absorption of the excited state is different than that of the ground state, the photoacoustic signal indicates the relative population of the excited and ground states. By changing the time delay between the pulses, the decay of the excited state population can be monitored and the excited state lifetime can be extracted. The wavelengths of the two pulses are independently optimized to maximize contrast. The excitation wavelength is chosen to match the absorption peak of the dye in its ground state to efficiently excite the dye. The optimal wavelength of the photoacoustic probing pulse maximizes the difference of ground state vs. excited state absorption.

Figure 1A:
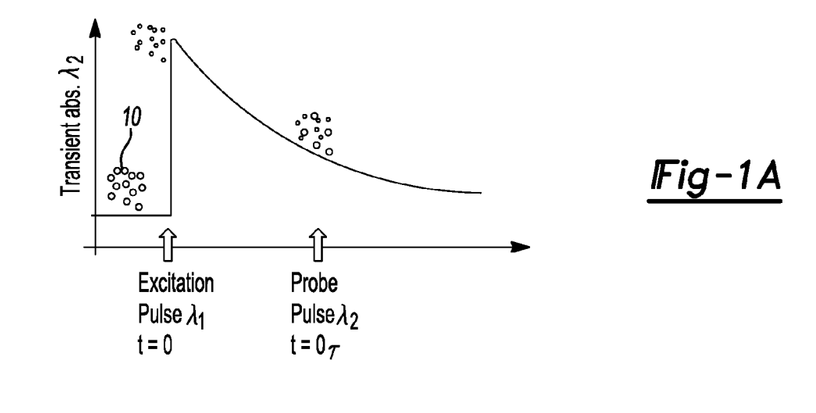
FIG. 1A illustrates principles of photoacoustic lifetime measurement of a phosphorescent oxygen sensitive dye according to the principles of the present teachings.
Figure 1B:
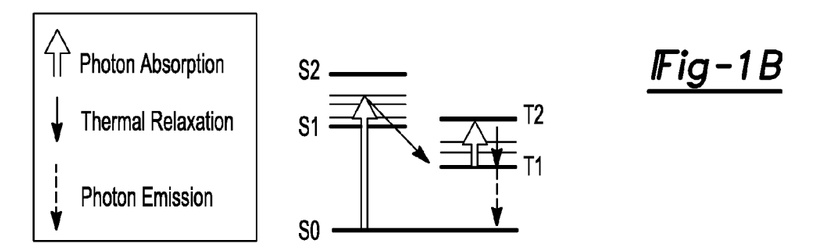
FIG. 1B illustrates a photoacoustic lifetime measurement process according to the principles of the present teachings.

A schematic illustration of the principle of operation of the present teachings is provided in FIGS. 1A and 1B. That is, FIGS. 1A and 1B illustrates the principles of photoacoustic lifetime measurement of a phosphorescent oxygen sensitive dye according to the principles of the present teachings. Dye molecules at ground state (open circles) 10 are excited at t=0 (closed circles) by a short laser pulse of wavelength $\lambda_1$ (532 nm in this work). The dye molecule is excited to its first singlet state (S1) and then to a triplet state (T1) by internal system crossing. This process is relatively efficient (quantum yield of 50% for PtOEP dye) and occurs in a time scale of picoseconds. Population of the T1 excited state then decays back to ground state via phosphorescence and quenching by collisions with oxygen molecules. The decay rate is relatively slow (~50 μs for PtOEP) and depends on oxygen concentration in the environment. A probe pulse (at 740 nm in this work) fired at t=τ generates a photoacoustic response due to optical absorption corresponding to T1→T2 transition. The absorption is transient because of the decay of the population of the T1 state. The amplitude of the photoacoustic signal generated at different delay times τ is used to measure the decay rate of the T1 excited state population.

The method of the present teachings is well suited for tissue imaging because both the excitation and photoacoustic probing pulses are insensitive to light scattering, while the generated acoustic waves propagate with minimal scattering and provide useful information for image reconstruction.

To demonstrate these new principles, a Pt(II) octaethylporphine (PtOEP: Frontier Scientific Inc.) oxygen sensitive dye was used. Its excited state has intrinsically long lifetime (91 μs in polystyrene medium), however, it decreases in the presence of oxygen due to inter-molecular collisions resulting in energy transfer to the oxygen molecule. Measuring the lifetime, therefore, yields a measure of the concentration of oxygen.

Figure 2:
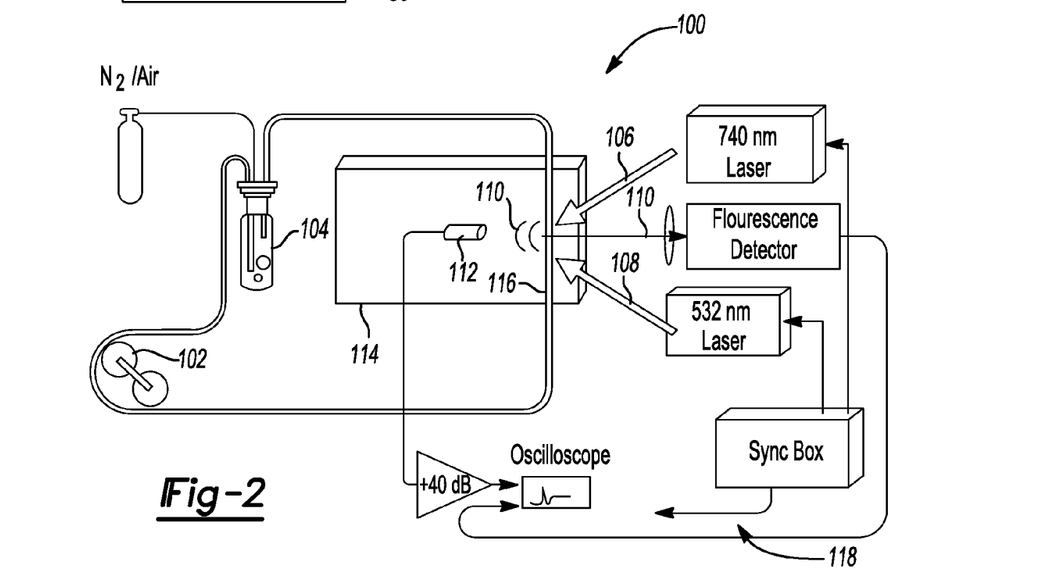
FIG. 2 illustrates an experimental setup having a closed flow circulating dye, in plastic tubing, a peristaltic pump, and an oxygenation cell.

Referring to FIG. 2, an experimental setup 100 is provided having a closed flow circulating dye, in plastic tubing 116, a peristaltic pump 102, and an oxygenation cell 104. The excitation 106 and probe 108 beams illuminate a section of tubing 116. Photoacoustic signals 110 are detected by a focused ultrasound transducer 112. Water tank 114 is used for ultrasound coupling between the tubing 116 and the transducer 112. Time-dependent fluorescent signal is detected by a photodetector and recorder 118 using a digital oscilloscope.

Experimental setup 100 consists of a closed flow system for circulating the dye and controlling the concentration of dissolved oxygen, and two pulsed lasers for excitation and photoacoustic probing. The air tight closed flow circulation system includes 0.8 mm ID (3.8 mm OD) transparent plastic tubing (Tygon Lab R-3603, L/S13, Cole-Parmer), a compatible peristaltic pump (MasterFlex 7524-00, Cole-Parmer), and an air sealed gas exchange cavity for controlling the level of dissolved oxygen in the dye by either bubbling N2 or air, for low and high oxygen concentration respectively. A doubled YAG laser (QuantaRay, λ=532 nm, pulse energy=11 mJ, pulse width=12 ns, beam width=9 mm) was used for excitation. A doubled YAG laser pumped OPO system (Surelite I-20, Surelite OPOplus, Continuum, λ=740 nm, pulse energy with ND filters=10 mJ, pulse width=5 ns, beam width=4 mm) was used for photoacoustic probing.

The two laser beams were directed to overlap on a section of the circulating dye tubing. A focused ultrasound transducer (Panametrics V311, 10 MHz, f#1.5), focused at the beam overlap position, was used to detect the photoacoustic signal. The signal was amplified by a +40 dB amplifier (Panametrics 5072PR) and recorded by a digital oscilloscope (WaveSurfer 432, LeCroy Inc., bandwidth limited to 20 MHz, 20 averaging). The timing of the excitation and probing pulses was controlled by a programmable logic array that allows for an accurate time delay in the range of −100 μs to +400 μs between the excitation and the probe pulses. The dye was first dissolved in toluene at a 1 mM concentration of stock solution which was then diluted with ethanol to prepare a 100 μM dye solution. An optical system for collecting the fluorescence light was added to allow simultaneous measurement of fluorescence and photoacoustic signals. The optical system includes a collecting lens (f=50 mm, diameter=25 mm), band-pass filter (615/60 nm, Chroma, Technology Corp.), and a photodiode (FDS010 Si Photodiode, Rload=2.5 Kohm, Thorlabs Inc.).

The photoacoustic response for a set of excitation-probe time delays in the range of 0 to 100 μs was measured. This set of measurements was repeated after 120 minutes of N2 bubbling (low oxygen state) and after 10 minutes of air bubbling (high oxygen state). A reference signal with no excitation pulse, which corresponds to ground state constant absorption at the probe wavelength (740 nm), was also recorded for each oxygen state. The reference signal is subtracted from the measured photoacoustic signals at different delays to extract the contribution of transient absorption to the photoacoustic signals. An example of transient absorption photoacoustic signals at three different time delays and low oxygen state is illustrated in FIG. 3.

Figure 3:
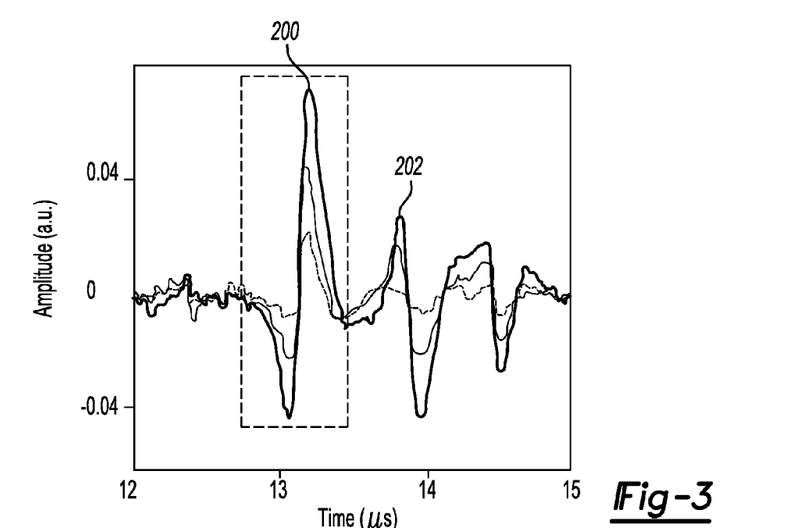
FIG. 3 illustrates a graph of photoacoustic signals at three different time delays (6, 34, and 100 μs), after a reference signal that corresponds to infinite time delay (no excitation) was subtracted.

With continued reference to FIG. 3, the graph illustrates photoacoustic signals at three different time delays (6, 34, and 100 μs), after a reference signal that corresponds to infinite time delay (no excitation) was subtracted. The signals were measured at low oxygen level. The rectangular frame (dashed line) indicates the time window used for signal processing. The first 200 and second 202 peaks in the signals correspond to the front and back dye-tubing interfaces.

Figure 4:
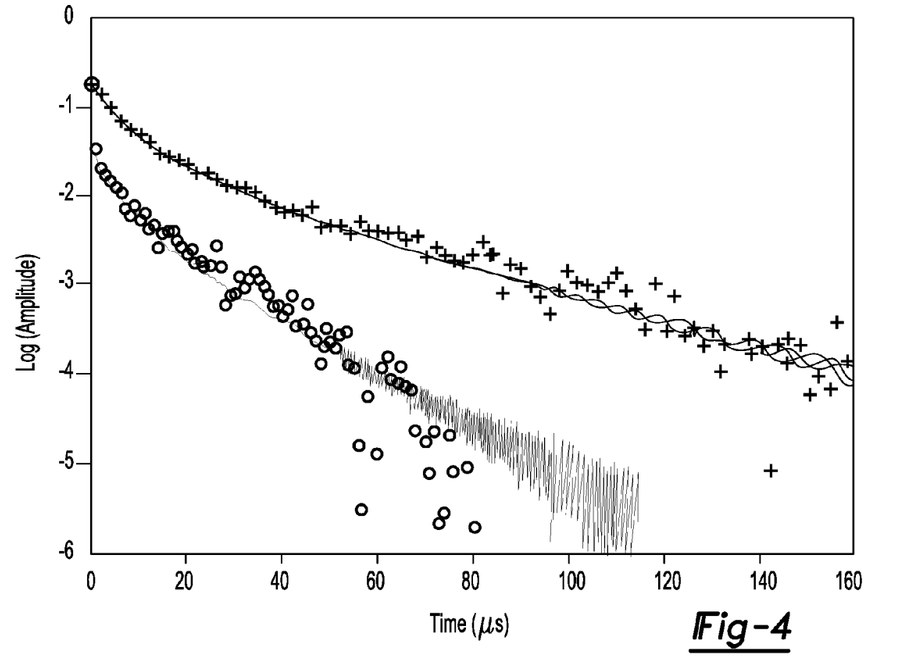
FIG. 4 is a graph illustrating the comparison of excited state lifetime measured by photoacoustic method and time resolved fluorescence at two oxygen levels, including photoacoustic low oxygen level (+), photoacoustic high oxygen level (o), fluorescence low oxygen level, and fluorescence high oxygen level.

Still referring to FIG. 3, to measure the amplitude of the signals, the square root of the signal energy in a time window containing the first peak was calculated. The photoacoustic signal amplitudes, of both low and high oxygen states, as a function of the excitation-probe delay time are shown in FIG. 4. To compare the excited state lifetime based on the photoacoustic (PA) measurements with fluorescence lifetime (FL), the fluorescence emission was collected. The photoacoustic and fluorescence lifetimes were measured by fitting an exponential decay function to data in the range of 4 to 30 µs. A close agreement is found between lifetimes measured in both methods. The results are summarized in Table 1.

TABLE 1

|  | Method | Lifetime (µs) |
|---|---|---|
| Low $O_2$ | PA | 33.1 ± 2 |
|  | FL | 33.2 ± 0.2 |
| High $O_2$ | PA | 11.3 ± 0.7 |
|  | FL | 13.9 ± 0.2 |

The results for the high oxygen state show significant deviation from a simple exponential decay. This deviation is primarily due to lack of dynamic range in the photoacoustic measurement.

In the current work we have used green light (532 nm) to excite the dye, which has very shallow tissue penetration (less than 2 mm). To translate the method to medical applications it is beneficial to replace the dye with a red or NIR excitable dye. A potential candidate is Pd-tetra-(4-carboxyphenyl) tetrabenzoporphyrin dendrimer (PdTBP) (Oxygen enterprises Ltd, Philadelphia, Pa.) which can be excited at 630 nm. To estimate the effective penetration depth in tissue we first calculate the optical fluence required for saturated absorption as: $I_{sat} = h\nu/\sigma$, where h is Planck's constant, $\nu$ is the optical frequency and $\sigma$ is the single molecule cross-section for absorption. For PdTBP dye this requirement yields a value of 1.5 mJ/cm2. Considering tissue effective attenuation at a wavelength of 630 nm, and assuming surface illumination of 20 mJ/cm2 (complying with ANSI Z136.1 laser safety standard), efficient excitation would be achieved up to a depth of 2 cm. At larger depths, partial dye excitation would result in decreased contrast and a larger error in the evaluation of dye lifetime. The actual depth limit for oxygen imaging should be determined experimentally, since it depends on the specific noise characteristics of the signal acquisition system.

The present teachings provide a new technique for quantifying excited state lifetime of a dye, based on photoacoustic probing. The technique is demonstrated by measuring different lifetimes of an oxygen sensitive dye that is subjected to different oxygen concentrations. The results obtained by the photoacoustic method were verified by an independent measurement of the lifetimes by conventional time-dependent fluorescence.

Still further, the local photoacoustic measurement technique can be extended to lifetime imaging by replacing the single ultrasound transducer with an ultrasonic array receiver and acquisition system. Photoacoustic lifetime imaging can overcome some of the difficulties associated with applying fluorescent lifetime imaging in clinical diagnosis. First, deeper penetration in tissue will be achieved, since the excitation pulse and the probe pulse only traverse a single path to the target, while fluorescent measurement requires two way light propagation. The typical penetration depth for photoacoustic imaging, at a wavelength of 740 nm, exceeds 5 cm 9. However, effective dye excitation imposes an additional limitation on the penetration depth. In the near infrared (NIR) region this would correspond to a depth of 2-3 cm. Second, high image resolution can be maintained up to the full penetration depth. Unlike fluorescence imaging, photoacoustic imaging is not degraded by the strong optical scattering in tissue. In addition, 3D imaging (with 2D receiver arrays) is possible.

In some embodiments, the present teachings can use a long excitation pulse. This long excitation pulse can be shorter than the resolution required for lifetime measurement. In our example, a 1 µs excitation pulse could be used to measure the long lifetime (10 to 90 µs) of PtOEP dye. The advantage of using a relatively long excitation pulse is that photoacoustic signals generated by this pulse (corresponding to fast thermal relaxation) would have low frequency content, easily rejected by a high-pass filter, thus leaving photoacoustic signals of the probe pulse free of interferences.

Developing the technique for clinical tissue pO2 imaging could provide a valuable tool for cancer diagnostics, staging and treatment monitoring. Over the past decade, studies have demonstrated high correlations of hypoxia with tumor aggressiveness and tumor resistance to therapy. Delivering the dye to tumor in-vivo is a challenging task. One of the promising ways to accomplish it, is using dye nano-encapsulation technology such as PEBBLE (Probing Explorers for Bioanalysis with Biologically Localized Embedding). It allows for specific tissue targeting by biocompatible nanoparticles embedded with the sensor dye. The method may also find utilization for imaging in turbid environmental media.

Our specific implementation of the photoacoustic lifetime measurement relied on the fact that the lifetime is in the order of 10's of microseconds, much longer than the laser pulse width. However, most fluorophores in biological systems (or those used to probe biological systems) have lifetimes shorter than the 5 ns laser pulse width. In principle, the method can be scaled to measure shorter lifetimes by using laser pulse widths that are shorter than the required lifetime measurement resolution (e.g picosecond lasers). In this case the resulting photoacoustic signal would combine contributions from the excitation pulse and the delayed probe pulse (transient absorption). The decay of the photoacoustic signal amplitude as a function of the excitation-probe delay time would still reflect the transient absorption. However, penetration depth would be compromised due to lower pulse energy in picosecond lasers, lower efficiency for photoacoustic generation and reduced contrast due to large constant absorption term. In spite of these difficulties, we believe that photoacoustic probing of excited state decay in the nanoseconds range of endogenous species (e.g. hemoglobin) and functional exogenous molecular probes would open up a range of new applications for medical molecular imaging.

In sum, a new method was developed to perform local measurements of fluorophore excited state lifetimes in turbid media without collecting the fluorescence emission. The method is based on a pump-probe approach where a first laser pulse excites the dye and then a second laser pulse is used for photoacoustic probing of the transient absorption. The photoacoustic response generated by the probe pulse is recorded by an ultrasound receiver. Repeating the measurement for increasing pump-probe time delays yields a series of photoacoustic signals which are used to extract the lifetime of the excited state. The method was validated by measuring the lifetime of an oxygen sensitive dye solution at different concentrations of dissolved oxygen. The dye was pumped with a 532 nm pulsed laser and the transient absorption at 740 nm was probed using a second pulsed laser system. The photoacoustic based results are in close agreement with those obtained from time-dependent fluorescent measurements. The method can be extended to photoacoustic lifetime imaging by using a receiver array instead of a single receiver.

Potential applications of this method include: tissue oxygen imaging for cancer diagnostics and mapping molecular events such as resonant energy transfer and ion collisions in a biological environment.

B. pH Imaging Technique

More than a century after the discovery of the photoacoustic phenomenon by Alexander Graham Bell in 1881, with the development of high power pulsed lasers, photoacoustic sensing and imaging has emerged as a sensitive analytical technique that can be applied to both industrial and medical applications. Its implementation for medical imaging has been intensively investigated during the last decade. It is an attractive modality for early cancer screening and detection in vivo, and both in vitro and in vivo imaging of vasculature and tissues. As discussed herein, the technique relies on short laser pulse illumination, creating rapid heating and acoustic emission due to thermal expansion of light absorbing components. An ultrasonic array is used to detect the emitted acoustic field and reconstruct the initial heat distribution. We report here a chemical/biochemical sensing/tissue imaging application.

Interest in this technique for sensing and imaging in turbid media, such as tissue, is due to the hybrid nature of the technique where the imaging contrast is based on the distribution of optical absorption, and the spatial resolution of the image is based on ultrasound imaging. Low ultrasound scattering in tissue allows for high, diffraction limited, resolution. Photoacoustic imaging depth is governed by light propagation in tissue. High penetration can be achieved in the "tissue transparent" spectral window between 700 nm to 1100 nm. It has been reported in the literature that photoacoustic imaging (at 800 nm) has produced sub-millimeter image resolution at an imaging depth of 5.2 cm in tissue when optically matched contrast agents (Indocyanine Green dye) are used to enhance the photoacoustic signal of embedded objects in tissue.

Fluorescent dye indicators have been widely used in biological research for exploring cells, tissues, and small animals. In conjunction with fluorescentmicroscopy they can provide intra and intercellular mapping. Specific fluorescent dye indicators have been developed for probing ionic analytes such as $H^{+6}$ and $Ca2+$, and molecular analytes such as O2 and NO.

Figure 5:
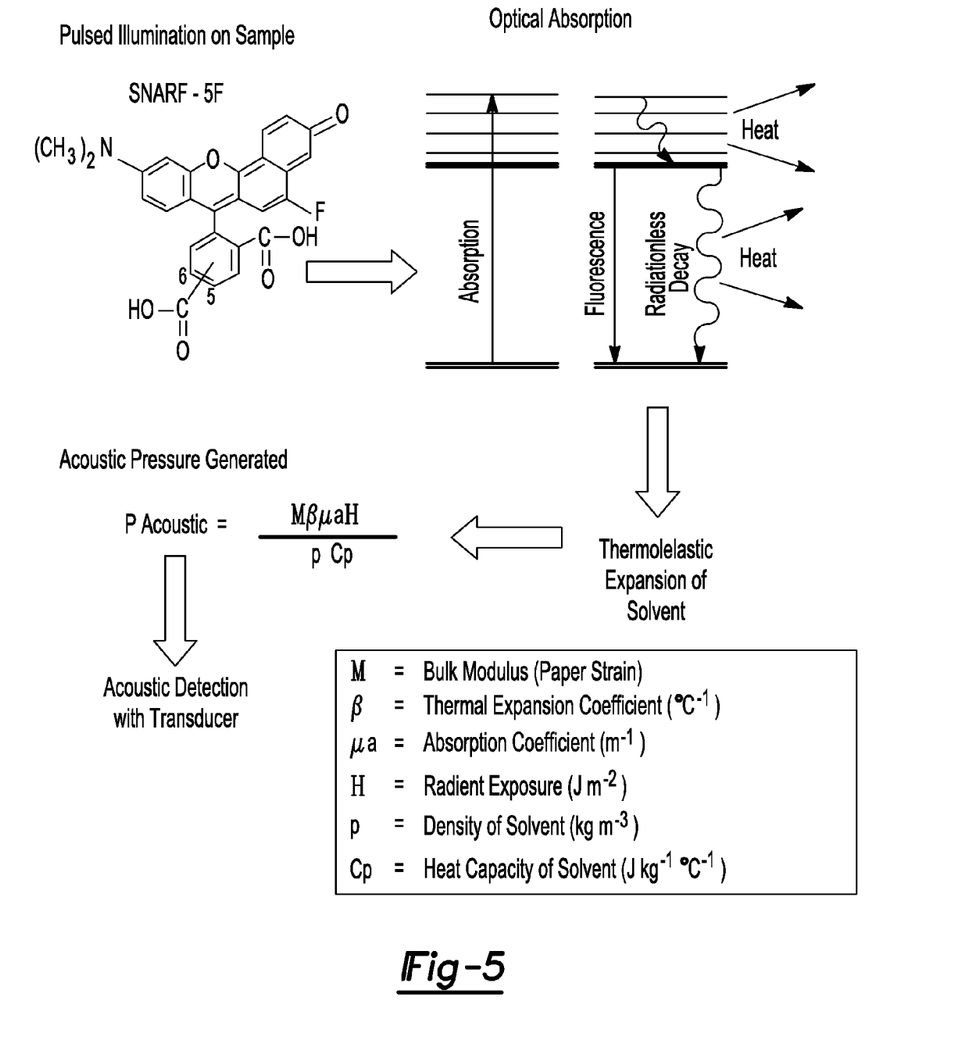
FIG. 5 illustrates principles of the generation of a photoacoustic wave by the optical absorption of light.

With the advent of photoacoustic imaging, the use of absorption and fluorescence based indicators can potentially be extended to clinical non-invasive functional imaging. The interaction of the dye indicator with the analytes can change the absorption of light by the dye, its fluorescent emission, or both. In any case, the non-radiative energy relaxation is altered, giving rise to a change in the photoacoustic signal generation (see FIG. 5). Therefore the indicator acts as a "sonophore", i.e. a molecular indicator whose sonic response is dependent on analyte concentration.

The goal of this work is to improve upon conventional non-ratiometric photoacoustic pH measurement method, in an industrial context, and thus to be able to move toward a biomedical imaging modality where pH can be measured in intact tissue. The experimental design is based upon an optical system that allows ratiometric photoacoustic detection of pHus-ing the fluorescent pH indicator dye, seminaphthorhodafluors-5F (SNARF-5F) (Invitrogen, Inc., Eugene, Oreg., USA). The SNARF-5F dye lends itself perfectly to be used as a ratiometric pH sonophore for our optical setup, because of the selfreferencing isosbestic point of the indicator dye near 532 nm (wavelength of the double YAG laser), and the pH sensitive absorption peak near 580 nm (excited with the emission of a dye laser).

Figure 6:
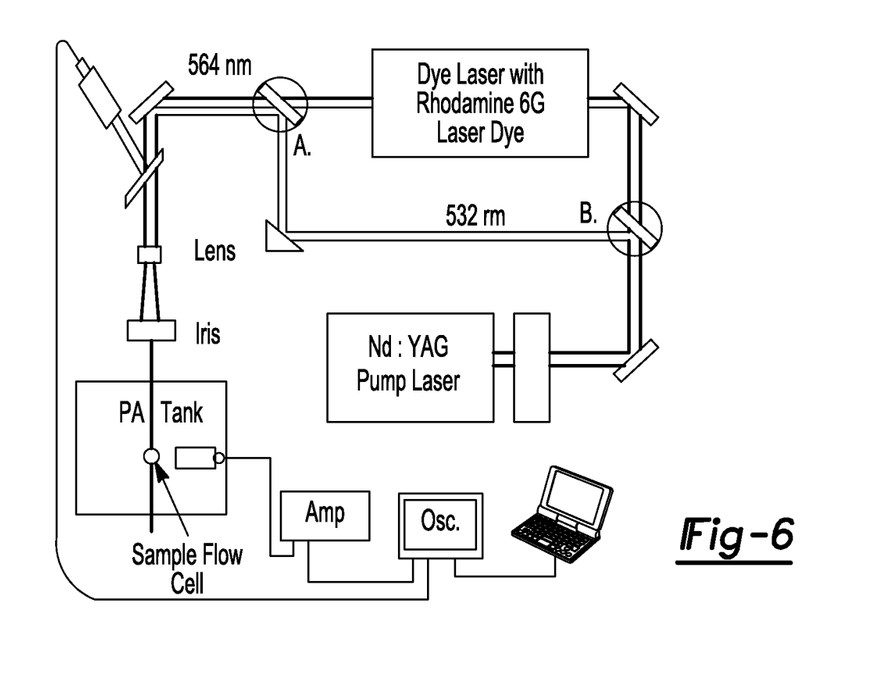
FIG. 6 illustrates an experimental setup of an optical system used to measure the ratiometric photoacoustic response for SNARF-5F dye as a function of pH.
Figure 7:
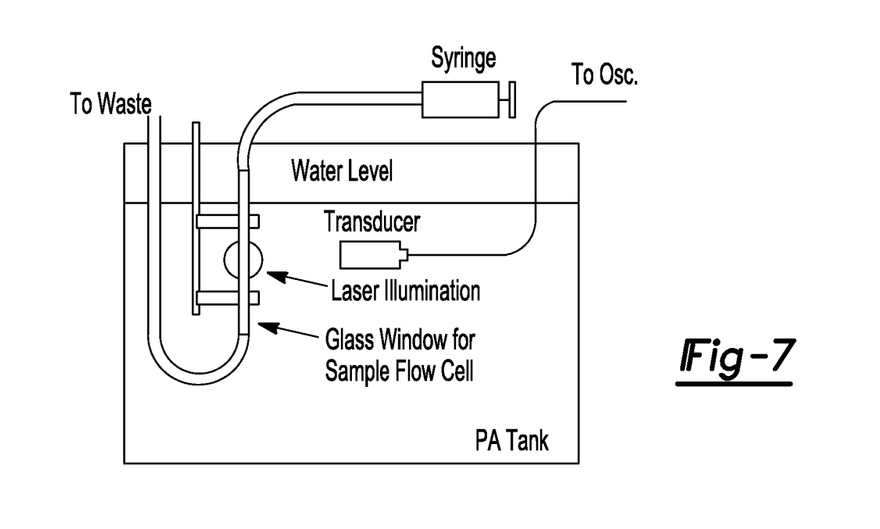
FIG. 7 is an enlarged cross-section view of the photoacoustic tang in FIG. 6.

The dye laser system used for the optical set-up was a Lambda Physik, Lasertechnik Scanmate R_dye laser that was pumped with a frequency doubled Surelite I10 Continuuum-R_Nd:YAG laser (420 mJ, 10 Hz repetition rate, emission at 532 nm) (see FIGS. 6 and 7). The laser dye that was used for the experiment was rhodamine 590 chloride (Exciton, Inc., Dayton, Ohio, USA), which was dissolved in methanol (Sigma-Aldrich, St. Louis, Mo., USA) and excited at 532 nm. The emission from the dye laser was set to 564 nm, to excite the pH sensitive region of the absorption spectrum of the SNARF-5F dye.

To excite the pH insensitive isosbestic point near 532 nm, a set of repositionable mirror mounts were used to redirect the 532 nm emission of the pump laser along the same path as the 564 nm light from the dye laser system. The 532 nm excitation was used to excite the photoacoustic response at the isosbestic point, acting as an internal reference for each sample.

The system was set up using two ultrasound transducers, one for photoacoustic detection and the other for normalization of the laser pulse energy. The normalization transducer was a 5 MHz flat transducer that was used to detect thermoacoustically generated waves induced by light absorption on its front face. A glass slide was placed in the beam paths for both lasers so the reflection of both beams could be used to normalize laser emission for both the 532 nm and the 564 nm laser beams. The detection transducer that was used to detect the photo-generated acoustic signal from the sample was an Aerotech 3.5 MHz transducer with a 1.9 cm aperture and a 10 cm focal length. This transducer was submerged under water in the acoustic tank and positioned about 10 cm from the sample.

A sample flow cell was constructed for this experiment using a piece of glass tubing as a sample window with two pieces of nylon tubing attached to each end. One side of the nylon tubing was fitted with a plastic insert that was used to attach a syringe for sample introduction. The other end of the tubing was left long enough to allow for transport of waste out of the acoustic tank. When setting up the tank, a solution of red food coloring was pushed into the sample cell and illuminated with the pulsed laser excitation. The transducer's position was then adjusted until the photoacoustic signal from the food coloring was maximized on the oscilloscope.

The signal from the detection transducer was amplified with a Panametrics 5077PR Pulser/Receiver. The signal amplification was set to 50 dB, with both the high pass (1 MHz) and the low pass (10 MHz) filters operating. The amplified signals, from both the detection transducer and the normalization transducer, were collected using a LeCroy Wavesurfer 432, 350 MHz Oscilloscope. Channel one was set to 10 mV/Division, DC 50× coupling, and 20 MHz bandwidth. Channel two was set to 100 mV/Division, DC 50× coupling, and 20 MHz bandwidth. Both channels were set to take an average of 20 acquisitions. The time setting for the oscilloscope was 10 IS/Division.

The photoacoustic samples were prepared by diluting an aliquot of a SNARF-5F stock that was prepared in a pH 6.0, 0.05 M phosphate buffered solution (Sigma-Aldrich, St. Louis, Mo., USA). Sample solutions were made at pH 6, 7, 8, and 9 using the appropriate buffered solutions. The final concentration of the SNARF-5F indicator dye in each pH buffered solution was 43.2 IM.

The photoacoustic response was measured for each pH solution by aliquotting four samples for each solution. Each measurement of the photoacoustic response, for each specific sample, was an average of 20 acquisitions of the acoustic response of the sonophore indicator dye in order to reduce the noise in the measurement. The order of the measurements for the 16 total trials was performed in random order to observe the reproducibility of the measurements for each pH. The photoacoustic pH measurements were conducted by injecting 0.5 mL of the sample solution into the sample flow cell and adjusting the position of the sample solution plug with an air bubble that was pushed into the tubing with the syringe. When the sample reached the glass sample window on the flow cell, its motion through the tube was stopped and the measurement was taken.

Figure 8:
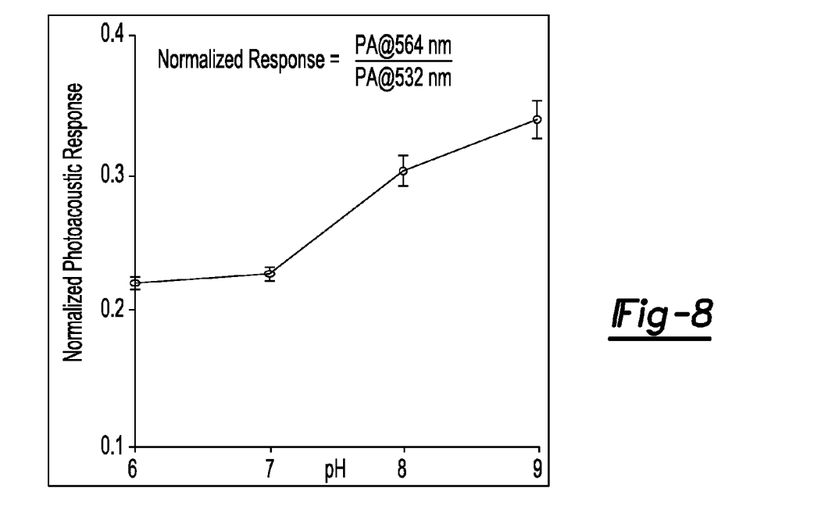
FIG. 8 is a normalized photoacoustic response calibration plot for SNARF-5F pH sonophore dye solution, wherein the concentration of the dye in the photoacoustic measurement was 43.2 μM and the error bars represent the relative error propagated for the ratio of the photoacoustic response at 564 nm with respect to that of the photoacoustic response at 532 nm for the four independent measurements.
Figure 9:
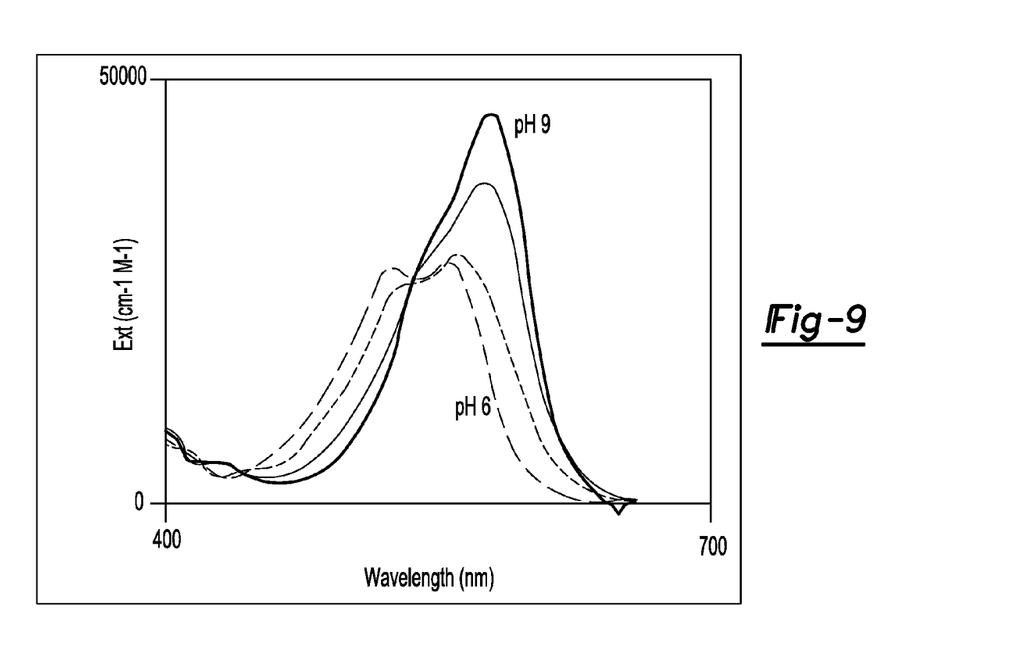
FIG. 9 illustrates that as the pH is increased from pH 6 through pH 9 for 10 μM SNARF-5F dye samples, the extinction at 564 nm increases as the pH increases and the extinction at 532 nm remains the same as the pH is increased from pH 6 to pH 9 for the four samples.

The results in FIG. 8 show that the ratiometric, photoacoustic response of the pH sensitive sonophore, SNARF-5F, is a monotonic function of pH with higher sensitivity in the 7-8 pH range. When illuminating the dye samples with the 532 nm pump laser excitation, near the isosbestic point of the dye, the overall photoacoustic response was relatively constant over the course of all the measurements. When the dye was excited at 564 nm, the photoacoustic response increased as a function of pH, which matches the expected result because the pH indicator dye SNARF-5F exhibits an increase in absorption as the pH of the solution increases (see FIG. 9).

In conclusion, it has been shown that when using SNARF-5F as a pH sensitive sonophore, organic indicator dyes can be used as a photoacoustic sensor/contrast agent for pH sensing and imaging. In order to utilize this method for in vivo pH imaging in tissue, NIR absorbing dyes will have to be utilized to increase penetration depth in tissue. This method can also be generalized to be used with nanoparticle "PEBBLE" sensors, 10,11 to cover a wider range of analytes and to enable targeting to specific in-vivo locations.12 Research areas of interest where this experimental technique would be directly applicable would be analytical biochemistry measurements of pH in whole intact tissue or in in vivo animal models. With careful selection of sonophores, this technique could apply to the detection and diagnosis of disease states that alter the pH, or other analytes of interest, in tissue or biological fluids. Specific examples include cancer, inflammation and diseases associated with gastric acidity.

In other words, a new method to perform local measurements of fluorophore excited state lifetimes in turbid media without collecting the fluorescence emission is provided. The method is based on a double pulse illumination where a first laser pulse excites the dye and then a second laser is used for photoacoustic probing of the transient absorption. The photoacoustic response generated by the probe pulse is recorded by an ultrasound receiver. Varying the time delay between excitation and probing allows for tracking the relaxation dynamics of the excited state. The method was validated by measuring the lifetime of an oxygen sensitive dye (Pt(II) octaethylporphine) solution at different concentrations of dissolved oxygen. The dye was excited with a 532 nm pulsed laser and the transient absorption at 740 nm was probed using a second pulsed laser system. The photoacoustics based results coincide with those obtained from simultaneous time-resolved fluorescent measurements. The method can be extended to photoacoustic lifetime imaging by using a receiver array instead of a single receiver. This opens unique possibilities for non-invasive, clinical functional imaging. For example, combined with oxygen sensitive dye, 3D imaging of tissue oxygenation could be developed for accurate diagnosis of cancer tumors, better planning of radiation therapy, and monitoring efficacy of treatment. Other potential applications include: in-vivo mapping of ion (e.g. Ca) concentration and dynamics and imaging of enzymes activity and metabolic functions, as well as environmental studies in turbid media.

What is claimed is:

1. A method of measuring fluorophore excited state lifetimes comprising:
    initiating a first excitation pulse at a dye at a first time point to excite dye molecules of said dye from a ground state to an excited state;
    initiating a first probing pulse at said dye molecules thereby generating first photoacoustic waves at a second time point;
    collecting said first photoacoustic waves after said initiation of said first probing pulse;
    analyzing said first photoacoustic waves relative to a first time delay between said first time point and said second time point to determine a first intensity point;
    initiating a second excitation pulse at said dye at a third time point to excite dye molecules of said dye;
    initiating a second probing pulse at said dye molecules thereby generating photoacoustic waves at a fourth time point;
    collecting said second photoacoustic waves after said initiation of said second probing pulse;
    analyzing said second photoacoustic waves relative to a second time delay between said third time point and said fourth time point to determine a second intensity point; and
    determining a slope between said first intensity point and said second intensity point.

2. The method according to claim 1 wherein said initiating a first excitation pulse at a dye at a first time point to excite dye molecules of said dye from a ground state to an excited state comprises initiating said first excitation pulse at said dye at said first time point to excite dye molecules of said dye from said ground state to an excited singlet state, said dye molecules then relaxing to a first vibration band and then through spin-orbit coupling crossing to a lower energy triplet state.

3. The method according to claim 2 wherein said initiating a first probing pulse at said dye molecules thereby generating first photoacoustic waves at a second time point comprises initiating said first probing pulse at said dye molecules at an energy sufficient to excite only excited molecules of said dye molecules at a detectable amplitude.

4. The method according to claim 3 wherein said analyzing said photoacoustic waves relative to said first time point and said second time point to determine an excited state lifetime further comprises analyzing said detectable amplitude.

5. A method of measuring fluorophore excited state lifetimes comprising:
    initiating a first excitation pulse at a dye at a first time point to excite dye molecules of said dye from a ground state to an excited state;
    initiating a first probing pulse at said dye molecules thereby generating first photoacoustic waves at a second time point;
    collecting said first photoacoustic waves after said initiation of said first probing pulse;
    analyzing said first photoacoustic waves relative to a first time delay between said first time point and said second time point to determine a first intensity point;
    initiating a second probing pulse at said dye molecules thereby generating photoacoustic waves at a time of approximately ten times an expected lifetime of said dye molecules following said first time point to define an infinite time delay;
    collecting said second photoacoustic waves after said initiation of said second probing pulse;

analyzing said second photoacoustic waves relative to said infinite time delay to determine a second intensity point; and determining a slope between said first intensity point and said second intensity point.

6. The method according to claim 5 wherein said initiating a first excitation pulse at a dye at a first time point to excite dye molecules of said dye from a ground state to an excited state comprises initiating said first excitation pulse at said dye at said first time point to excite dye molecules of said dye from said ground state to an excited singlet state, said dye molecules then relaxing to a first vibration band and then through spin-orbit coupling crossing to a lower energy triplet state.

7. The method according to claim 6 wherein said initiating a first probing pulse at said dye molecules thereby generating first photoacoustic waves at a second time point comprises initiating said first probing pulse at said dye molecules at an energy sufficient to excite only excited molecules of said dye molecules at a detectable amplitude.

8. The method according to claim 7 wherein said analyzing said first photoacoustic waves relative to said first time point and said second time point to determine an excited state lifetime further comprises analyzing said detectable amplitude.

* * * * *

UNITED STATES PATENT AND TRADEMARK OFFICE
CERTIFICATE OF CORRECTION

PATENT NO. : 7,576,334 B2
APPLICATION NO. : 12/050493
DATED : March 18, 2008
INVENTOR(S) : Shai Ashkenazi et al.

It is certified that error appears in the above-identified patent and that said Letters Patent is hereby corrected as shown below:

Column 3, line 33, "illustrates" should be --illustrate--.

Column 5, line 28, "enterprises" should be --Enterprises--.

Column 7, line 60, "pHus-ing" should be --pH using--.

Column 7, line 61, "Oreg." should be --OR--.

Column 8, line 51, "DC 50x coupling" should be --DC 50 X coupling--.

Column 8, line 52, "DC 50x coupling" should be --DC 50 X coupling--.

Column 9, line 31, "locations. 12" should be --locations 12.--.

Signed and Sealed this

Ninth Day of February, 2010

David J. Kappos
*Director of the United States Patent and Trademark Office*